United States Patent [19]

Baglioni

[11] Patent Number: 4,666,936
[45] Date of Patent: May 19, 1987

[54] AMIDE DERIVATIVES OF 2-(P-AMINOBENZYL)-BUTYRIC ACID AND ESTERS THEREOF HAVING HYPOLIPIDEMIZING ACTIVITY

[75] Inventor: Alessandro Baglioni, Rome, Italy

[73] Assignee: Medosan Industrie Biochimiche Riunite S.p.A., Italy

[21] Appl. No.: 763,246

[22] Filed: Aug. 7, 1985

[30] Foreign Application Priority Data

Aug. 14, 1984 [IT] Italy .................. 48728 A/84

[51] Int. Cl.⁴ ............... A61K 31/40; A61K 31/19; C07D 207/327; C07C 101/66
[52] U.S. Cl. .................. 514/427; 514/417; 514/533; 514/563; 548/476; 548/563; 560/48; 560/47; 562/457
[58] Field of Search .............. 548/476, 563; 562/457; 560/48; 514/417, 427, 563, 533

[56] References Cited

U.S. PATENT DOCUMENTS

| | | | |
|---|---|---|---|
| 3,629,450 | 12/1971 | Gruenfeld et al. | 514/563 |
| 3,793,458 | 2/1974 | Wermuth et al. | 514/563 |
| 3,804,839 | 4/1974 | Dahm et al. | 548/563 |
| 4,207,341 | 6/1980 | Hubner et al. | 560/48 |
| 4,238,506 | 12/1980 | Stach et al. | 514/563 |
| 4,316,850 | 2/1982 | Carney et al. | 548/476 |

FOREIGN PATENT DOCUMENTS

| | | | |
|---|---|---|---|
| 1006959 | 1/1976 | Japan | 548/476 |
| 504434 | 4/1971 | Switzerland | 548/563 |

OTHER PUBLICATIONS

Chapman, J. Med. Chem. vol. 26, pp. 237–241 (1983).
Turner et al., Screening Methods in Pharmacology, vol. II, pp. 121–140.
Zimmermann, Atherosclerosis, vol. 29, pp. 477–485 (1978).
Hasson, Clofibrate, pp. 197–216 (1984).

Primary Examiner—Mary E. Ceperley
Attorney, Agent, or Firm—Cushman, Darby & Cushman

[57] ABSTRACT

Amide derivatives of 2-(p-aminobenzyl)-butyric acid and esters thereof having a hypolipidemizing and hypocholesterolemizing pharmaceutical activity and their preparation are described.

Included are compounds of the formula

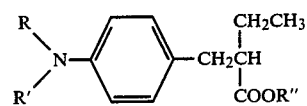

wherein R and R' together represent the group

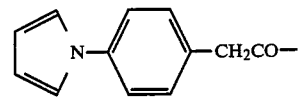

or the group

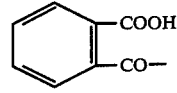

and R" is hydrogen or a 1 to 6 carbon alkyl group.

9 Claims, No Drawings

AMIDE DERIVATIVES OF 2-(P-AMINOBENZYL)-BUTYRIC ACID AND ESTERS THEREOF HAVING HYPOLIPIDEMIZING ACTIVITY

FIELD OF THE INVENTION

The present invention relates to amide derivatives of 2-(p-aminobenzyl)-butyric acid and esters thereof having the general formula (1)

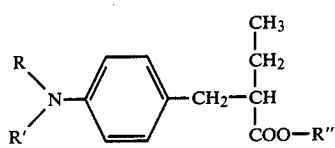

wherein R, R' together represent the group

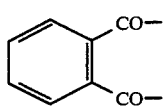

or R is a hydrogen atom and R' represents a group

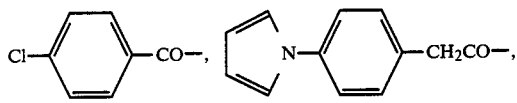

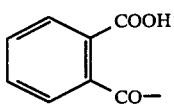

and R" is a hydrogen atom or a 1 to 6 C alkyl group, preferably an ethyl group.

Said compounds can all be structurally derivatives from 2-(p-aminobenzyl)-butyric acid through amidation of the amine group and they form a novel class of hypocholesterolemizing and hypolipidemizing agents.

DESCRIPTION OF THE PRIOR ART

Drugs having a hypolipidemizing activity are known.

Among these Fenbutyramide, Xenbucin and β-benzalbutyric acid can be cited, having the formula, respectively

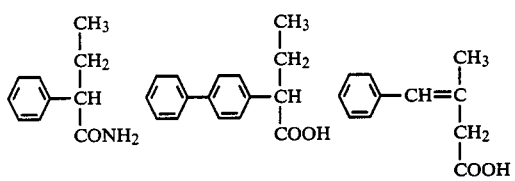

The above drugs however show a low activity.

It is also known from the literature (Chapman J. M. et al, J. Med. Chem. 26: 237–243; 1983) that phthalimide and the derivatives thereof show hypocholesterolemizing activity, which however has not led to a commercial use due to the low level of such activity.

It is also known that Bezafibrate

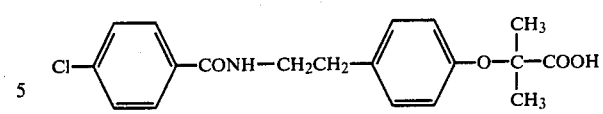

and Clofibrate

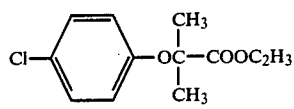

have the ability to decrease the hematic levels of cholesterol and triglycerides (see R. Zimmerman et al: Atherosclerosis 29: 477; 1978; M. M. A. Hassan, A. A. Elazzouny: Analytical Profiles of Drug Substances vol. 11; K. Florey, Ed. Academic Press New York; 1982, pages 197–224).

Among the phthalimide derivatives, o-(N-phthalimido)acetophenone

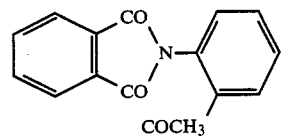

has been found to be more active than Clofibrate in reducing the serum cholesterol percentage and the triglyceride level. The o-(N-phthalimido)-acetophenone activity appears to occur possibly in various ways, of which the inhibiting activity in vivo is cited on the hepatic enzymes involved in the biosynthesis de novo of the triglycerides and moreover the ability to speed up the excretion of cholesterol with the bile and to decrease the cholesterol absorption at the intestinal level.

Additional hypolipidemizing drugs of interest are Procetofene of formula

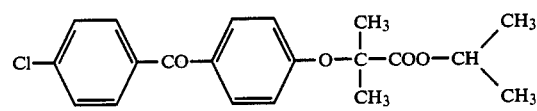

as well as the compound

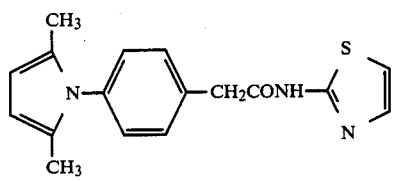

which show a hypolipidemizing activity lower than that of Bezafibrate.

SUMMARY OF THE INVENTION

The compounds of formula (1) which are an object of the present invention, have shown to have a hypocholesterolemizing as well as hypolipidemizing activity higher than that of Bezafibrate and Clofibrate, together with an extraordinary low toxicity which makes said compounds extremely interesting from a therpeutic viewpoint.

Accordingly, object of the present invention are the compounds of formula (1) as well as pharmaceutical compositions for lowering the lipid and cholesterol level in blood, containing a pharmaceutically effective amount of said compounds.

DETAILED DESCRIPTION OF THE INVENTION

The compounds corresponding to formula (1) wherein group R(R')N— is a phthalimide group are represented by 2-(p-phthalimidobenzyl)-butyric acid of formula (2)

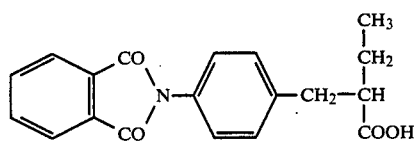

and the ethyl ester thereof of formula (3)

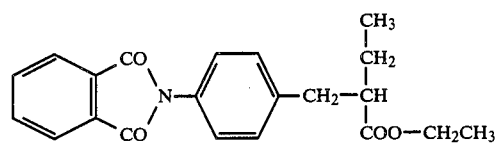

Further amide derivatives according to the present invention correspond to formulae (4), (5) and (6)

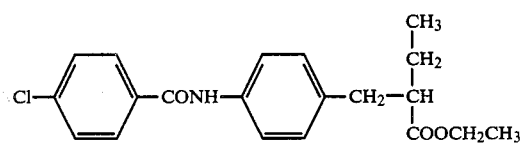

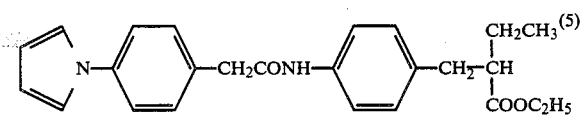

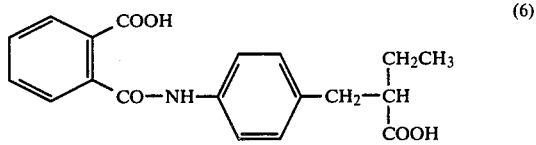

The compounds (2), (3), (4), (5) and (6) show a particularly high hypocholesterolemizing and hypolipidemizing activity, as confirmed by pharmacological tests, the results of which are referred to hereinafter.

Compound preparation

The preparation of compounds (2), (4) and (5) was carried out starting from 2-(p-aminobenzyl)-butyric acid ethylester, as obtained by cathalytic reduction with hydrogen in the presence of 10% Pd/C of 2-(p-nitrobenzyl)-butyric acid ethylester, as described in the chemical literature (Lellman, E. Scheich C., 20, 438, 1887). Ethyl-2-(p-aminobenzyl)-butyrate forms the ethylester (3) by a fusion treatment with phthalic anhydride. This reaction can also be carried out in suitable high-boiling solvents in the presence of dehydrating agents, if any.

The preparation of compound (4) was carried out starting again from ethyl 2-(p-aminobenzyl)-butyrate by reaction with p-chlorobenzoic acid chloride in anhydrous THF and in the presence of triethylamine. This reaction could also be carried out in a protic or aprotic medium in the presence of an organic or inorganic base depending on the medium which is used.

The amidation of ethyl-2-(p-aminobenzyl)-butyrate with 4-(1-pyrryl)phenylacetic acid to obtain the ester (5) was effected in anhydrous THF in the presence of N,N'-carbonyldiimidazole.

Acid (3) was obtained by alkaline saponifcation of ester (2) with 4% aqueous sodium hydroxide. Compound (6) was formed as an intermediate which provides acid (2) by heating above the melting point.

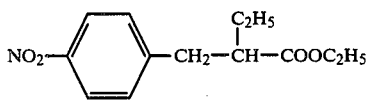

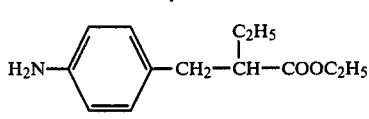

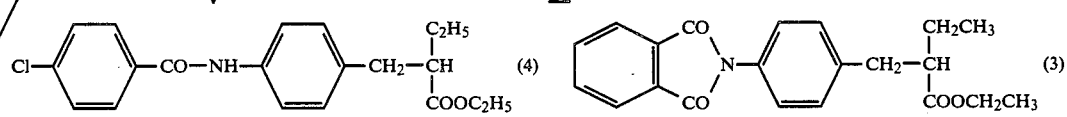

-continued

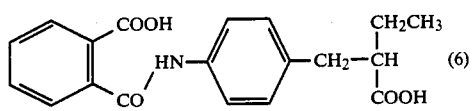

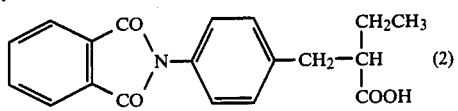

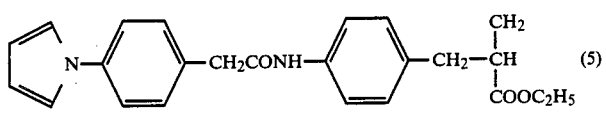

EXAMPLES OF PREPARATION

The preparation of compounds (2), (3), (4), (5) and (6) was practically effected as referred hereinafter:

EXAMPLE 1

Preparation of 2-(p-aminobenzyl)-butyric acid ethyl ester 28 g of 2-(p-nitrobenzyl)-butyric acid ethyl ester are dissolved in 200 ml ethyl acetate. The solution is added with 1 g of 10% Pd/C and hydrogenated in a Parr apparatus until complete absorption of hydrogen. After filtering and evaporation from solvent about 25 g of product are obtained as a sufficiently pure oil for the successive reactions.

EXAMPLE 2

Preparation of 2-(p-phthalimidobenzyl)-butyric acid ethyl ester (compound 3)

A mixture of ethyl-2-(p-aminobenzyl)-butyrate (4.4 g) and phthalic anhydride (3 g) is heat melted until ceasing of water evolution (5 minutes). After cooling, the solid as obtained is crystallized from ethanol. Yield: 4.8 g (68.6%); m.p. 86°–87° C. Analysis:

$C_{21}H_{21}NO_4$ (351.39) calc. %: C 71.78; H 6.02; N 3.99; found: C 71.64; H 6.19; N 4.10.

EXAMPLE 3

Preparation of 2-(p-phthalimidobenzyl)-butyric acid (compound 2)

A suspension of ethyl-2-(p-phthalimidobenzyl)-butyrate (4.2 g) in 18 ml NaOH 1N is reflux heated for one hour. After decoloration on bone black, the solution is made acidic with concentrated HCl. The so separated oil is extracted with ethyl acetate dried on anhydrous $Na_2SO_4$. By solvent evaporation a solid is obtained which, when recrystallized from benzene-ethyl acetate (1:1), provides 1.7 g of a compound with m.p. 133°–135° C. Such compound is 2-(p-phthalylaminobenzyl)-butyric acid (compound 6). Analysis:

$C_{19}H_{19}NO_5$ (341.35) calc. %: C 66.75; H 5.61; N 4.10; found %: C 66.98; H 5.57; N 4.16.

This acid, by heating above the melting point, is transformed into 2-(p-phthalimidobenzyl)-butyric acid (compound 2) after crystallisation from aqueous ethanol. Analysis:

$C_{19}H_{17}NO_4$ (323.33) calc. %: C 70.56; H 5.30; N 4.33; found: C 70.85; H 5.57; N 4.16.

EXAMPLE 4

Preparation of 2-[4-(p-chlorobenzamido)-benzyl]-butyric acid ethyl ester (compound 4).

A solution of ethyl-2-(p-aminobenzyl)-butyrate (3.3 g) and triethylamine (1.5 g) in anhydrous THF (70 ml) is slowly (10 minutes) addioned with a solution of p-chlorobenzoylchloride (2.6 g) in 30 ml of anhydrous THF. It is stirred for an hour at room temperature, then filtered and the solution as obtained is vacuum evaporated. The obtained solid residue is crystallized from methanol providing 4 g amide with m.p. 119°–120° C. Analysis:

$C_{20}H_{22}ClNO_3$ (359.89) calc. %: C 66.74; H 6.17; Cl 9.85; N 3.89; found: C 66.44; H 6.21; Cl 9.78; N 4.01.

EXAMPLE 5

Preparation of 2-{4-[4-(1-pyrryl)-phenylacetamido]-benzyl}-butyric acid ethyl ester (compound 5).

A solution of 4-(1-pyrryl)phenylacetic acid (3 g) in anhydrous THF (50 ml) is additioned with a solution of carbonyldiimidazole (2.9 g) in THF (80 ml). After 45 minutes a solution of ethyl-2-(p-aminobenzyl)-butyrate (3.3 g) in THF (30 ml). is added. It is reflux heated for an hour, then dried and the residue is dissolved in dichloromethane. The organic solution is washed, first with NaOH 1M, then with HCl 1M and lastly with water. After drying on anhydrous sodium sulfate it is filtered and dried. A yellow solid (1.4 g) is obtained which melts at 100°–102° C. Analysis:

$C_{25}H_{28}N_2O_3$ (404.49) calc. %: C 74.23; H 6.98; N 6.93; found: C 74.28; H 6.97; N 7.01.

PHARMACOLOGICAL PROPERTIES

From tests effected with amide derivatives of 2-(p-aminobenzyl)-butyric acid and the esters thereof corresponding to the general formula (1), it results that such compounds have pharmacological properties suitable for therapeutic utilization in some pathological conditions. In particular the experimental tests have been effected with the compounds (2), (3), (4), (5) and (6).

The preparations administered "in vivo" by oral route, comprise a 0.5% suspension of carboxymethylcellulose in a neutral pH normal physiological saline for the compounds (3), (4) and (5), while for the compounds (2) and (6) the preparation comprises a solution in NaOH (0.1N) at pH 7–7.5.

The compounds of the invention have shown a high hypolipidemizing activity.

This pharmacotherapeutic effect was obtained with dosages and methods of administration which have not caused significant toxic effects.

The hypolipidemizing activity was compared with Bezafibrate and Clofibrate.

HYPOLIPIDEMIZING ACTIVITY

The hypolipidemizing activity of the substances under test was evaluated as the ability to decrease the hematic levels of triglycerides and total cholesterol in animals made hyperlipidemic by administration of Triton (antihyperlipidemic agents, J. N. Moss, Screening Methods in Pharmacology, Ed. Robert A. Turner and P. Hebborn, volume II, Academic Press, pages 121–143).

The test was carried out on two animal species: rat and mouse. Male Wistar rats and Swiss mice were used, held at a normal diet, the former weighing 200–260 g, the latter weighing about 26–30 g.

The compounds (2), (3), (4), (5) and (6) and the Bezafibrate and Clofibrate of control were administered per os at a dose of 500 mg/kg, simultaneously with a 10% solution in normal saline of Triton WR-1339 endoperitoneally at a rate of 2 ml/kg body weight.

After treatment, the animals were divided into lots of eight, and held fasting for 18 hours and then sacrificed. The hematic levels of triglycerides total cholesterol are measured on the serum by enzymatic methods (Test-Combination Triglycerides, Boehring Mannheim GmbH) and and colorimetric methods (Test-Combination Cholesterol, Boehring Mannheim GmbH). The results on the hypolipidemizing activity of the compounds under test in rat and mouse are referred in tables I and II.

TABLE I

Hypolipidemizing activity in rate of the amide derivates of 2-(p-aminobenzyl)-butyric acid and esters thereof:

| Compounds | Total cholesterol | | Triglycerides | |
|---|---|---|---|---|
| | % mg | % variation | % mg | % variation |
| Carrier | 270 | — | 520 | — |
| Bezafibrate | 210 | −22 | 415 | −20 |
| Clofibrate | 218 | −19 | 420 | −19 |
| Compound (2) | 176 | −35 | 360 | −31 |
| Compound (3) | 189 | −30 | 390 | −25 |
| Compound (4) | 200 | −26 | 400 | −23 |
| Compound (5) | 205 | −24 | 410 | −21 |
| Compound (6) | 180 | −32 | 380 | −28 |

TABLE II

Hypolipidemizing activity in mouse of the amide derivatives of 2-(p-aminobenzyl)-butyric acid and esters thereof:

| Compounds | Total cholesterol | | Triglycerides | |
|---|---|---|---|---|
| | % mg | % variation | % mg | % variation |
| Carrier | 209 | — | 147 | — |
| Bezafibrate | 139 | −33 | 100 | −32 |
| Clofibrate | 152 | −27 | 115 | −22 |
| Compound (2) | 130 | −38 | 60 | −59 |
| Compound (3) | 140 | −33 | 64 | −56 |
| Compound (4) | 129 | −38 | 90 | −39 |
| Compound (5) | 130 | −38 | 80 | −45 |
| Compound (6) | 130 | −38 | 64 | −56 |

TOXICITY $DL_{50}$ was evaluated after administration of the compounds (2), (3), (4), (5) and (6) alone in male albine Swiss mice weighing 27±3 g, using the oral route. The animals were held under observation by checking the mortality and pain signs, if any, for 15 days.

The $DL_{50}$ values (mg/kg) are referred in table III.

TABLE III

Acute toxicity in mouse of the amide derivatives of 2-(p-aminobenzyl)-butyric acid and esters thereof: compounds (2), (3), (4), (5) and (6).

| Compounds | $DL_{50}$ (mg/kg)/os |
|---|---|
| (2) | >2000 |
| (3) | >1700 |
| (4) | >2000 |
| (5) | >2000 |
| (6) | >2000 |
| Clofibrate | 1280[x] |

[x]Value as reported in literature: G. Metz et al, Arzneimittel Forschung, 27: 1173; 1977.

The data referred in tables I, II show the pharmacotherapeutic effect of the amide derivatives of 2-(p-aminobenzyl)-butyric acid and esters thereof, which are the object of the present invention.

The compounds (2), (3), (4), (5) and (6) show an interesting ability to decrease the hematic levels of cholesterol and triglycerides within the tested dosages and with respect to the control products.

The low toxicity (table III) of said compounds gives them a high therapeutic index. Indeed the acute toxicity values are by several factors higher than the values used for reaching pharmaceutically active dosages.

At the dosages and with the methods used and specified in the above tests, the administration to healthy animals has not brought about mortality at a long or short-term, nor evidence of toxic effects.

The results referred in tables I, II and III document the therapeutic interest of a pharmaceutical composition according to the invention.

The patients in need of a hypolipidemizing and hypocholesterolemizing pharmaceutical treatment will be orally administered with a pharmaceutical composition comprising an effective amount of a compound of formula (1).

The dosage of this compound will generally be comprised between about 200 and about 600 mg/kg body weight/day, although larger and smaller dosages can be administered by having regard to the age, weight and general conditions of the patient.

The compounds according to the invention can be administered in the form of tablets, capsules, solutions, suspensions, together with pharmaceutically compatible, non-toxic carriers and excipients.

I claim:

1. A compound having the formula:

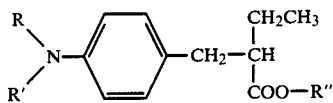

wherein R is hydrogen and R' represents the group

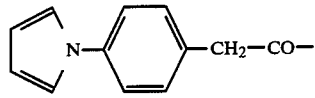

or the group

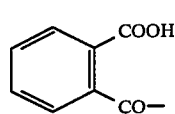

and R" is hydrogen or a 1 to 6 carbon alkyl group.

2. Compound according to claim 1, of formula

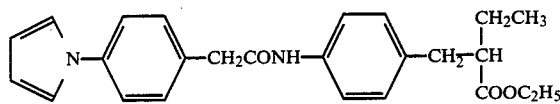

3. Compound according to claim 1, of formula

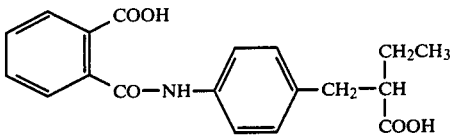

4. A hypolipidemizing and hypocholesterolemizing composition comprising an amount of a compound as recited in claim 1, pharmaceutically effective to decrease lipidemia and cholesterolemia and a pharmaceutically compatible carrier.

5. A method for reducing lipidemia and cholesterolemia in mammals comprising administering an amount of a compound as recited in claim 1, pharmaceutically effective to reduce lipidemia and cholesterolemia.

6. A compound according to claim 1 having the formula

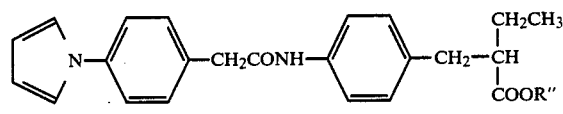

where R" is hydrogen or a 1 to 6 carbon alkyl group.

7. A method for reducing lipidemia and cholesterolemia in mammals comprising administering an amount of a compound as recited in claim 6, pharmaceutically effective to reduce lipidemia and cholesterolemia.

8. A method for reducing lipidemia and cholesterolemia in mammals comprising administering an amount of a compound as recited in claim 2, pharmaceutically effective to reduce lipidemia and cholesterolemia.

9. A method for reducing lipidemia and cholesterolemia in mammals comprising administering an amount of a compound as recited in claim 3, pharmaceutically effective to reduce lipidemia and cholesterolemia.

* * * * *